(12) United States Patent
Weindel et al.

(10) Patent No.: US 6,790,623 B2
(45) Date of Patent: Sep. 14, 2004

(54) DNA DETECTION BY MEANS OF A STRAND REASSOCIATION COMPLEX

(75) Inventors: Kurt Weindel, Wielenbach (DE); Joachim Brand, Peissenberg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 10/102,720

(22) Filed: Mar. 22, 2002

(65) Prior Publication Data

US 2003/0152937 A1 Aug. 14, 2003

Related U.S. Application Data

(63) Continuation of application No. 09/325,554, filed on Jun. 4, 1999, now Pat. No. 6,410,235.

(30) Foreign Application Priority Data

Jun. 4, 1998 (DE) .......................................... 198 24 900

(51) Int. Cl.[7] .......................... C12Q 1/68; C07H 21/02; C07H 21/04
(52) U.S. Cl. .......................... 435/6; 536/23.1; 536/24.3
(58) Field of Search .......................... 435/6, 91.2, 210; 536/24.3, 24.33; 935/77, 76, 78

(56) References Cited

U.S. PATENT DOCUMENTS

| | | | | |
|---|---|---|---|---|
| 4,683,202 | A | 7/1987 | Mullis | 435/91 |
| 5,344,757 | A | 9/1994 | Höltke et al. | 435/6 |
| 5,476,769 | A | 12/1995 | Söderlund et al. | 435/6 |
| 5,763,175 | A | 6/1998 | Brenner | 435/6 |
| 6,214,545 | B1 | 4/2001 | Dong et al. | 435/6 |
| 6,410,235 | B1 * | 6/2002 | Weindel | 435/6 |

FOREIGN PATENT DOCUMENTS

| | | |
|---|---|---|
| DE | 38 07 994 | 9/1988 |
| DE | 40 41 608 | 6/1992 |
| EP | 0 079 139 | 5/1983 |
| EP | 0 324 474 | 1/1989 |
| WO | 92/20702 | 11/1992 |
| WO | 95/00530 | 1/1995 |
| WO | 95/14706 | 6/1995 |
| WO | 95/25538 | 9/1995 |
| WO | 97/47640 | 12/1997 |

OTHER PUBLICATIONS

Voloshin et al., "*Chemical Probing of Homopurine–Homopyrimidine Mirror Repeats in Supercoiled DNA*", Nature, vol. 333, pp. 475–476, 1988.

Beal et al., "*Second Structural Motif for Recognition of DNA by Oligonucleotide–Directed Triple–Helix Formation*", Science, vol. 251, pp. 1360–1363.

Belotserkovskii et al., "*Formation of Intramolecular Triplex in Homopurine–Homopyrimidine Mirror Repeats With Point Substitutions*", Nucleic Acid Research, vol. 18, No. 22, pp. 6621–6624, 1990.

Roberts et al., "*Specificity and Stringency in DNA Triplex Formation*", Proc. Nat'l Acad, Sci. vol. 88, pp. 9397–9401, Nov. 1991.

Erhardt et al., "*Quantitative Assay of PCR–Amplified Hepatitis B Virus DNA Using a Peroxidase–Labelled DNA Probe and Enhanced Chemiluminescence*", Journal of Microbiology, vol. 34 (8), pp. 1885–1891.

Kaye et al., "*A Microtitre Format Point Mutation Assay: Application to the Detection of Drug Resistance in Human Immunodeficiency Virus Type–1 Infected Patients Treated With Zidovudine*", Journal of Medical Virology, vol. 37, pp. 241–246.

Stratagene Catalog, p. 39.

* cited by examiner

*Primary Examiner*—Ethan Whisenant
(74) *Attorney, Agent, or Firm*—Arent Fox PLLC

(57) ABSTRACT

The discriminating capability of hybridization assays is increased by a combination of labelled primers which produce amplificates of one strand of a nucleic acid with a capture probe which is complementary to the same strand of the nucleic acid.

11 Claims, 4 Drawing Sheets

FIG.3

```
507
Gly Thr Ser Gln Leu Ser Gln Phe Met Asp Gln Asn Asn Pro Leu Ser Gly Leu Thr His Lys Arg Arg Leu Ser Ala Leu Gly Pro
GGC ACC AGC CAG CTG AGC CAA TTC ATG GAC CAG AAC AAC CCG CTG TCG GGG TTG ACC CAC AAG CGC CGA CTG TCG GCG CTG GGG CCC
5'                                                                                                              3'
        511              516                      [Pro]            [Val]          526          [Tyr]  531      [Leu]
                         [CCG]                    [CTC]                           [TAC]                         [TTG]
                         "R1a"                    "R2"                            "R4a"                         "R5"
                                                                                  [Asp]
                                                                                  [GAC]
                                                                                  "R4b"
                                                                                  [Arg]
                                                                                  [CGC]
                                                                                  "dS4"

REGION #1          REGION #2          REGION #3          REGION #4          REGION #5
```

DNA DETECTION BY MEANS OF A STRAND REASSOCIATION COMPLEX

This is a Continuation of application Ser. No. 09/325,554 filed Jun. 4, 1999, now U.S. Pat. No. 6,410,235. The disclosure of the prior application(s) is hereby incorporated by reference herein in its entirety.

The invention concerns a method for the detection of nucleic acids using the amplification of the nucleic acid with the aid of labelled primers and detection of the amplificate with the aid of a capture probe.

Biospecific binding assays which enable the detection of certain analytes or analyte characteristics by means of molecular recognition mechanisms have become indispensable in diagnostics and bioanalytics. In this connection hybridization assays have become firmly established in recent years in addition to immunoassays and receptor ligand assays. Hybridization assays utilize the principle of nucleobase pairing (A::T; G:::C) for the molecular recognition of certain analyte nucleic acids (e.g. DNA, RNA) by probes with the desired specificity. Thus for example oligonucleotide probes which are composed of 18–20 nucleotides in a chosen sequence enable unequivocal detection even over the entire human genome.

Hybridization assays (=probe based assays) have been given an interesting and promising extension by so-called NA chip technologies. In these at least 2 and usually several to very many probes with different sequences and thus different specificity are bound in a geometric pattern in separate areas on a test carrier so that a corresponding number of hybridization reactions between the probes and nucleic acid analyte segments or different nucleic acid analytes can be carried out concurrently. Under suitable reaction conditions e.g. sequence selection, buffer environment, salt content and above all the incubation and wash temperature, it is possible to keep only those hybridization complexes bound to the solid phase in which all the nucleotides contained in the oligonucleotide probe are complementary to the corresponding nucleotides in the analyte molecule resulting in the full binding strength. This is then referred to as complete base pairing (perfect match, PM).

Hybridization complexes which contain mismatches (MM) are detached under such conditions. Under optimal conditions it is even possible to unequivocally distinguish between complexes with complete base pairings and complexes with 1-point mismatches (single base transitions). Since this occurs concurrently on the solid phase when using a geometric pattern of capture probes (array), it is referred to as probe array testing.

The capture probes can all have a constant length (number of nucleotide building blocks) or the oligo length can be inversely proportionally matched to the GC content. In the first case a common melting temperature Tm can be achieved for all completely paired hybridization complexes by buffer additives which for example strengthen AT bonds to such an extent that the Tm is independent of the nucleobase sequence and is only dependent on the oligo length. Examples of such additives are tetramethylammonium chloride (TMAC) and tetraethylammonium bromide. In the second case the stated length adaptation results in a Tm levelling. The capture probes can have chemically different backbones which carry the specificity-mediating nucleobases e.g. deoxyribosyl-phosphodiester strands (=>DNA), ribosyl-phosphodiester strands (=>RNA) or they can belong to a non-natural class of substances e.g. N-(2-aminoethyl)-glycyl or N-(2-aminoethyl)glutamyl strands (=>PNA, WO 92/20702).

Probe array testing is of interest for many molecular biological or diagnostic applications. These include multipathogen testing (simultaneous detection of different pathogens on a gene level), (sub)typing of organisms, analysis of genetic diversity (polymorphisms, mutations), sequencing of genes or genomes etc.

Nucleic acids are relatively complex analytes which usually have to be firstly isolated, then amplified and, in the case of DNA, rendered single-stranded (denatured) before they can be used in a probe based assay or probe array testing. This processing and the fact that complementary nucleobases also have a tendency for base pairing within one and the same strand result in some typical difficulties such as a variable analyte titre in the reaction solution due to variations in the efficiency of the isolation or amplification, a suboptimal denaturing efficiency, reassociation of the single strands of a DNA to form the original double strand which competes with the hybridization of a single strand with a probe, internal strand hybridization (formation of secondary structures e.g. hairpin loops or cross formations) which compete with the probe hybridization. This becomes more pronounced as the palindrome index increases i.e. the degree of self-complementarity of a DNA or RNA strand.

Especially the last two phenomena essentially determine the accessibility of the sequence region of the analyte which is the basis for the test and hence limit the overall performance of an entire array of capture probes.

The so-called PCR method (polymerase chain reaction, U.S. Pat. No. 4,683,202) is usually used to amplify the analyte nucleic acid. In this method it is possible to already incorporate a detectable group during the amplification e.g. a digoxigenin derivative (DIG-labelling, EP-B-0 324 474). This can be achieved by replacing a part of the dTTP by DIG-dUTP in the nucleoside triphosphate mixture.

A method is described in DE-A-3807994 (U.S. Pat. No. 5,476,769) in which detectably-labelled amplicon strands are hybridized to an immobilizable capture probe and the hybrids that are formed are detected.

The so-called sandwich hybridization method is described in EP-A-0 079 139 in which a nucleic acid to be detected is detected by hybridization with a capture probe and a detection probe which are complementary to different regions of the nucleic acid.

The object of the present invention was to improve hybridization assays which are based on a capture reaction of amplificates that have been generated while incorporating a label, in particular with regard to their discrimination between two or more nucleic acids with very closely related sequences.

A subject matter of the present invention is a method for the selective detection of a nucleic acid comprising the steps amplification of the nucleic acid or of a part thereof with the aid of two primers one of which can hybridize with one strand of the nucleic acid to be detected and the other can hybridize with a complementary strand thereto at least one of which contains a bound detectable label and to form each time an extension product of these primers in a reaction mixture, binding a capture probe to one of these extension products to form a hybridization complex which contains the capture probe and at least this extension product, separating the extension product bound to the capture probe from non-bound components of the reaction mixture and determining the detectable label bound to the capture probe wherein the capture probe is selected such that it can bind with the strand of the extension product which can also hybridize with the extension product formed by extension of the labelled primer.

Brief Description of the Drawings

FIG. 3 shows the position of several regions with mutations in a rpo β-gene segment.

Figure 1:
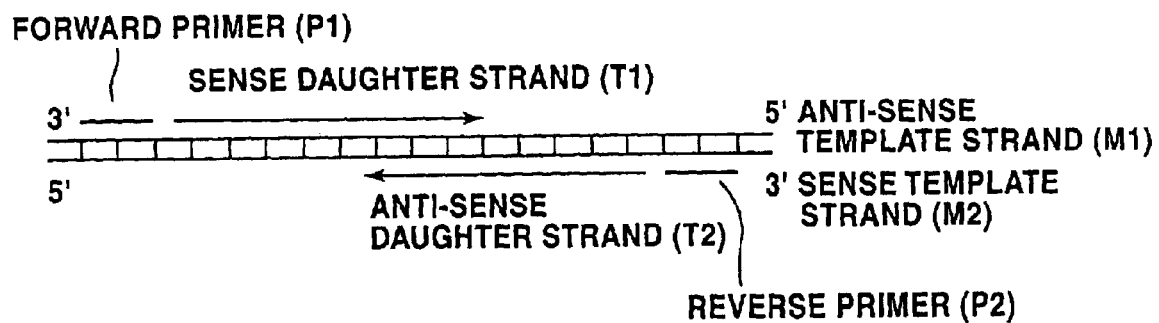
FIG. 1 shows schematically the individual components for amplification of the nucleic acid or a part thereof according to the invention.

The nomenclature of the individual components of the amplification as defined by the invention are shown schematically in FIG. 1. The meanings are as follows:

| | |
|---|---|
| P1 | forward primer |
| P2 | reverse primer |
| T1 | sense daughter strand (sense extension product) |
| T2 | anti-sense daughter strand (anti-sense extension product) |
| M1 | anti-sense template strand (template); strand of the nucleic acid to be detected |
| M2 | sense template strand (template); opposite strand to the nucleic acid to be detected |

Figure 2:
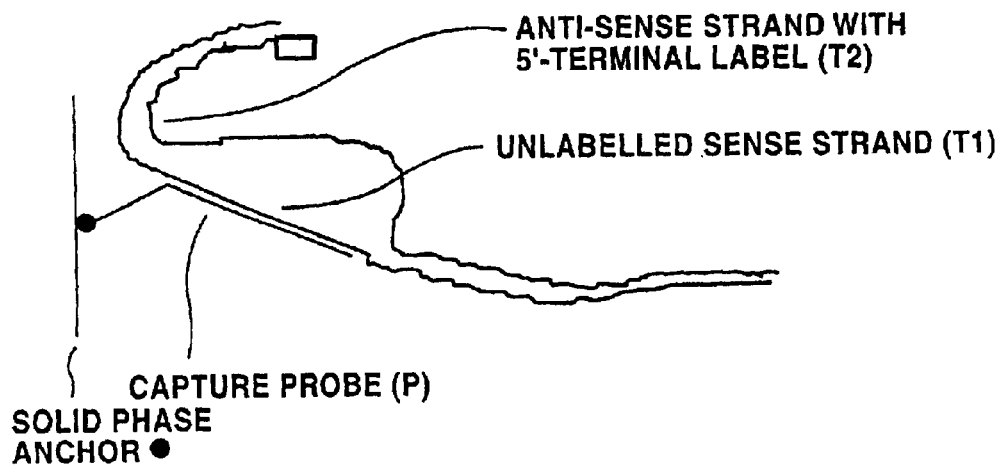
FIG. 2 shows schematically a complex comprising strand T1, strand T2 and capture probe P bound to a solid phase.

A complex that is already bound to the solid phase comprising the strands T1 (unlabelled), T2 (5′-terminally labelled) and the solid phase-bound probe P is shown schematically in FIG. 2. The rectangle is a detectable label.

The position of the regions with mutations in the segment is shown in FIG. 3.

Figure 4:
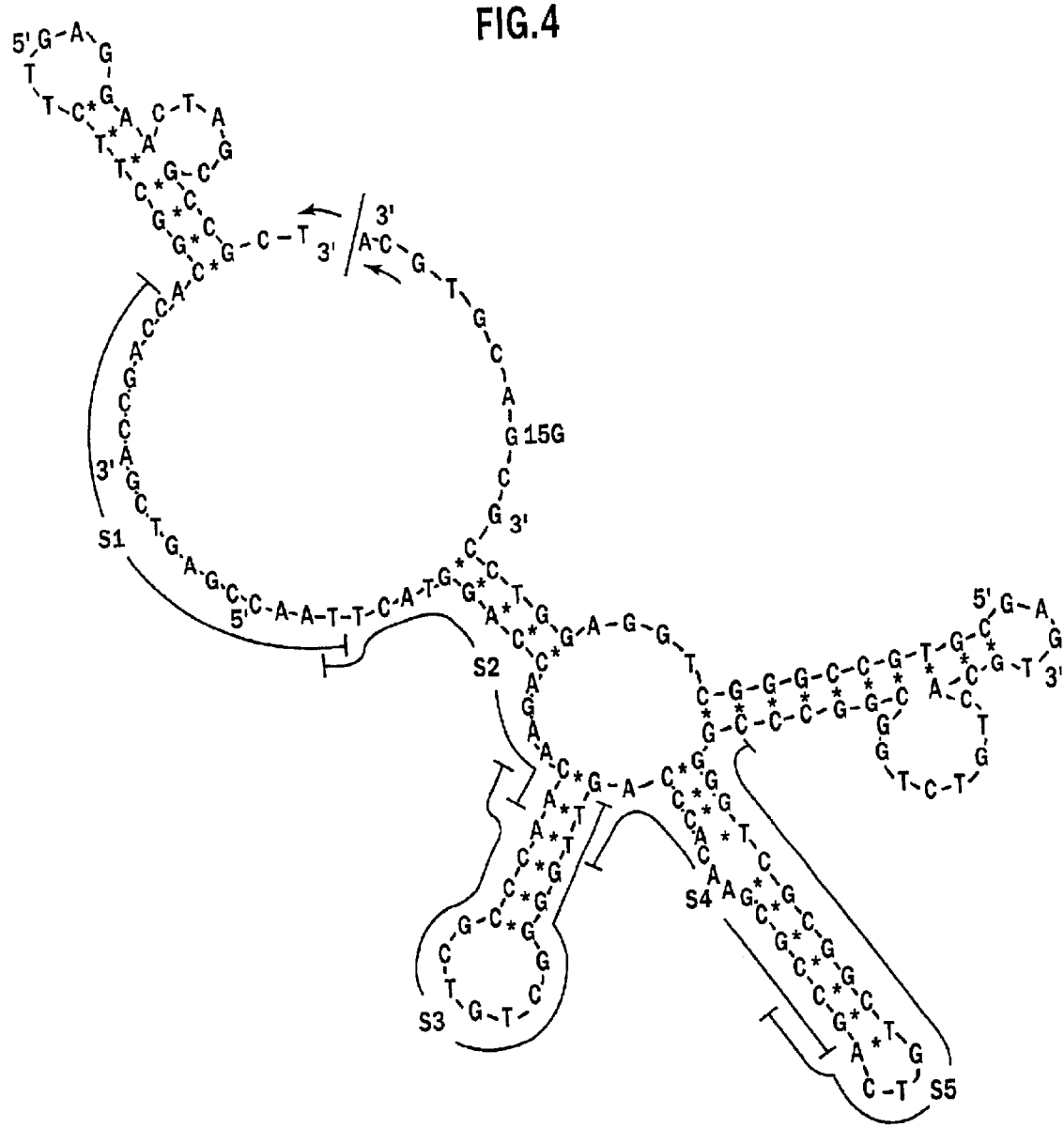
FIG. 4 shows a folding proposal for a rpo β-gene segment.

A folding proposal for the rpo β-gene segment is shown in FIG. 4.

Figure 5:
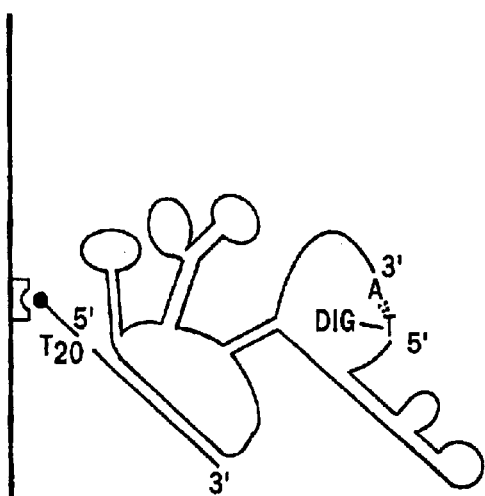
FIG. 5 compares the real situation A (folded DNA with internal strand association) and the ideal situation B (DNA with no internal strand association).

FIG. 5 shows a comparison between the ideal situation (rod-shaped DNA) and the real situation A (folded). It is clear that the accessibility of the terminal label is in fact greatly impaired. This impairment is reduced or avoided by the procedure of the present invention.

The core of the present invention is the surprising observation that the best discrimination power (differentiation between PM and MM) is achieved when the capture probes bound to the solid phase are designed to be complementary and anti-parallel to the sense strand which is synthesized in the PCR starting from an unlabelled forward primer, but the detection reaction is based on the anti-sense strand which is synthesized in the PCR starting from a reverse primer labelled with a detectable group so that the probe hybridization complex which determines the specificity (discriminating power) is detected indirectly and optionally quantified via the DNA strand reassociation complex. Conversely the capture probe can also be complementary to the anti-sense strand and detention is by means of reassociation with the sense strand that can be detected by the labelled forward primer.

Although this also has an effect on single hybridizations, it has a particularly positive effect in connection with hybridization assays carried out concurrently i.e. (D)NA probe array testing.

A selective test is understood as a test which selects and binds a nucleic acid with a target sequence that only differs slightly from a non-target sequence in a sample containing numerous nucleic acids that do not have the target sequence and among which the target sequence may be present. The binding occurs by pairing of complementary bases, such as A and T or U as well as G and C, of a probe and of the nucleic acid to be detected. For this purpose the sequence of the probe is highly complementary, preferably 100% complementary, to the target sequence of the nucleic acid especially with regard to those bases where the target sequence differs from the non-target sequences. The probe sequence is preferably between 8 and 36 nt, particularly preferably between 16 and 20 nt long. The chemical structure of the probe especially in the non-nucleobase part, e.g. the so-called backbone, can be relatively independently selected provided selective binding to the target sequence is still possible. In addition to the (preferred) oligonucleotides (the natural backbone or a sugar phosphate backbone modified by attaching groups serves as the backbone), the so-called peptide nucleic acids (PNA according to WO 92/20702, artificial amino acids incorporated into the structure of the backbone) have recently also proven to be suitable. Molecules with mixed backbone units are also suitable (WO 95/14706 or EP-A-0 672 700).

A capture probe whose function is to sequence-specifically immobilize the reaction complexes on the solid phase can for example bind to the strand of the extension product which can also hybridize with the extension product formed by extension of the labelled primer if it is complementary to a sequence on this extension product. This sequence is then the target sequence. This sequence of the nucleic acid to be detected is either known, can be determined by sequencing or is not defined and determined until it has bound to one or several capture probe(s) according to the invention.

The target sequence is preferably selected such that it is between the inner ends of the primers which face towards one another. The sequence of the target sequence is selected such that it differs from sequences of nucleic acids that are not to be detected especially with regard to its base sequence. The differences can for example be due to mutations (single or several base substitutions), deletions, insertions or polymorphisms.

A person skilled in the art can for example find suitable target sequences by sequence searches and sequence comparison in known sequence data bases. In the spirit of a preferred embodiment of the invention in which several sequences, sequence differences, mutations, polymorphisms or the like are detected, the target sequences are preferably within a region which can be amplified with the aid of a single primer pair (a reverse and a forward primer). However, in principle, it is also possible to use several primers especially when they all lead to amplificates which contain, among others, the regions corresponding to the other target sequences. The nucleic acid to be detected can be RNA or DNA of any desired origin. Genomic DNA is preferred.

A nucleic acid or sequence that is complementary to another nucleic acid or sequence is understood in this case as a nucleic acid or sequence which contains an uninterrupted, consecutive series of bases which can form Watson-Crick or/and Hoogsteen base pairings with an uninterrupted, consecutive series of bases of the other nucleic acid or sequence. This series is preferably longer than 10 bases.

A nucleic acid or sequence which is homologous to another nucleic acid or sequence is understood in this case as a nucleic acid or sequence which is complementary to a nucleic acid or sequence which is complementary to the other nucleic acid. In this process uninterrupted sequences of bases are compared in each case.

In this connection it is obvious to a person skilled in the art that there are also artificial bases in addition to the naturally occurring bases which do not differ significantly from the natural bases with regard to their ability to bind to other bases. In the case of oligonucleotides as probes this is also referred to as hybridization. The conditions under which an optimal hybridization occurs are familiar to a person skilled in the art. For example the temperature, probe length and salt content also depend on the GC content of the nucleic acid to be detected.

An advantage of the present method is that a higher selectivity of the detection can be achieved under otherwise identical conditions. On the other hand, the stringency of the process parameters (e.g. wash temperature) can be lowered while retaining the selectivity. Selectivity is understood as specific probe hybridization to nucleic acids with an exactly complementary base sequence while discriminating against all nucleic acids with a sequence that is not exactly complementary.

Samples within the sense of the invention are liquids such as body fluids, culture media or tissue, or products prepared therefrom such as lysates, extracts or isolates such as serum, plasma or products derived therefrom.

Methods for amplification are basically known to a person skilled in the art. Examples are amplifications such as NASBA (EP-B-0 329 822 or U.S. Pat. No. 5,130,238), LCR (EP-B-0 320 208) and PCR (WO 90/01069). However, amplification by the PCR principle (EP-B-0 200 362 or U.S. Pat. No. 4,683,202) is preferred within the sense of the invention. In this method at least two primers are used whose sequence is selected such that one can hybridize with a strand of the nucleic acid to be detected in such a way that, using this as a template and after the action of a polymerase and the other reagents necessary for this such as buffer, mononucleoside triphosphates etc, an extension product is formed using a nucleic acid segment as a template that is located downstream of the 3' end of the primer which in turn can serve as a template for hybridization with and extension of the other primer. The more selectively the primers bind to the nucleic acid or to its opposite strand, the more selective the amplification becomes. Numerous copies of the nucleic acid piece located between the outer ends of the primers which contains the target sequence(s) can be prepared by many repeats of the reaction steps: hybridization of the primer with its template, extension of the primer and separation of the extension product from its template.

A forward primer is understood as a primer which can or does hybridize with a sequence of the nucleic acid strand to be detected. The strand can be selected from one of the two strands of a double strand but it can also already be a single-stranded nucleic acid e.g. RNA, preferably mRNA or rRNA. The reverse primer is a primer which can or does hybridize with the extension product formed from the forward primer.

The forward primer is preferably a primer which can hybridize with the anti-sense strand of the nucleic acid to be detected, and the reverse primer hybridizes with the sense strand. Hence a sense extension product (sense daughter strand) is formed from the forward primer, FIG. 1.

In addition to a sequence which targets the primer binding site, the primers can also contain additional sequences which cannot directly hybridize with the nucleic acid to be detected such as oligo T ends which serve as spacers to a label preferably at the 5' end. The capture probes can also be modified in this manner.

Common primers have a length of between 12 and 30 nucleotides/bases. In the present invention these are both included in the subsequent detection which is an indication for the presence (qualitative test) or amount (quantitative test) of the analyte nucleic acid.

In the sense of the invention at least one but preferably only one of the primers selected from the group of forward and reverse primers and particularly preferably the reverse primer is detectably labelled. A label is understood as a chemical group whose properties differ in a detectable manner from those of nucleic acids. Such a property can for example be an absorbance at a particular wavelength, fluorescence, scattering, reflection or ability to bind to other substances. One can also divide them into direct and indirect labels. Direct labels can be detected as a result of their signal-generating property without the addition of further binding components. This group for example includes enzymes such as alkaline phosphatase or peroxidase (POD) which can be detected by monitoring the enzyme-catalysed conversion of a colour substrate. However, groups which fulfil these conditions are only preferred within the sense of the invention when the substrate remains in the vicinity of the complex during the measurement as is for example the case with aequorin. However, these also include signal-generating groups such as fluorescein which can be detected as a result of their spectral properties.

Indirect labels are those which require binding to an additional reagent which contains a component that can bind to them which can then in turn be directly or indirectly labelled. These groups include for example haptens such as biotin or digoxigenin. They can be detected by reaction with a detection reagent containing their binding partner e.g. streptavidin or an antibody; for this purpose they are labelled with a signal-generating or signal-mediating group such as aequorin or a fluorophore. Particulate components such as beads or microspheres made of latex which contain a detectable dye are particularly preferred as a signal-generating group. The invention has a particularly positive effect with particles of a large size which cannot bind to the label because of the steric situation shown in FIG. 5 (here the label is digoxigenin) if internal strand reassociation is not prevented. The label is of course expediently attached to the primer in such a way that it hinders as little as possible the hybridization and extension of the primer. In this connection it is preferable to attach it to the 5' end in the case of an oligonucleotide e.g. during the chemical synthesis using a phosphoramidite derivatized with the marker group. However, the label can also be attached to a base (WO 93/05060). In the case of PNA the label is preferably attached to the amino end (WO 92/20703).

A capture probe is understood as a unit which binds a nucleic acid, which can selectively bind one of the nucleic acid strands (extension products) produced by the amplification and can either be bound to a solid phase (immobilizable) or is bound to a solid phase (immobilized). In this connection a direct binding is understood as the binding of two bases with the aid of hydrogen bridges. Binding to a solid phase can be covalent or non-covalent. Covalent bonds can either be ensured by phosphodiester bonds (EP-B-0 386 229) and amide bonds (EP-B-0 562 025 or U.S. Pat. No. 5,242,974) or by activation of photosensitive residues (e.g. diazo groups) and contact with a solution in a probe which contains a reactive group (e.g. PCT/EP96/00893).

Non-covalent bonds are for example biospecific bonds such as those contained in the interacting pairs (strept) avidin-biotin, hapten-antibody, vitamin-receptor etc. The capture probe is preferably labelled with biotin e.g. via a 5' phosphate group with the aid of an aminoalkyl linker and the solid phase is coated with streptavidin. However, the capture probe is preferably already bound covalently or via a stable biospecific bond (e.g. (strept)avidin-biotin) to the solid phase before contact with the reaction mixture from the amplification. The constitution of the solid phase is not important for the present invention. However, it should be insoluble in the amplification mixture. Phases made of plastics with or without a metallic component e.g. in the form of beads or a porous fleece or a more or less flat, non-porous test carrier are for example particularly suitable. An important property of the carrier is that it represents a site at which the capture probes are bound or can be bound, and where the nucleic acid to be detected can bind if it is present. It is preferable not to use a capture probe which is 100% complementary to another capture probe at the same time.

A particular embodiment of the invention is directed towards the potential (multiple) detection of a plurality of nucleic acids with different sequences. This can be achieved by using a capture probe that is selective for each nucleic acid or sequence to be detected. Although the capture probes can be bound to different solid phases, they are particularly preferably bound to different sites and particularly preferably to defined geometric sites on the same solid phase that can be distinguished by the measurement technique preferably of the nucleic acid array type as described for example in WO 92/10588. In this connection it is possible to select certain geometric patterns such as rectangular, hexagonal or cross-shaped matrices which facilitate the evaluation. This enables the presence or absence of whole clusters of target sequences to be examined in a sample. The present invention utilizes the formation of a binding complex (hybrid) which contains the extension product of the reverse as well as of the forward primer and also the capture probe. In the following the extension product which has been formed by extension of the forward primer is referred to as the forward extension product. In the methods known from the prior art the required conditions have not been met for the measurable formation of such a hybrid. In general the formation of such a complex is favoured when the capture probe is given sufficient opportunity to hybridize with a strand of the amplificate before this can hybridize with its (amplificate) opposite strand to form a (re)association product. If this is not the case, the capture probe can no longer hybridize with the desired extension product especially in the case of nucleic acids to be detected which have a strong tendency for internal strand hybrid formation and the detection is impeded or made impossible since the signal strength is then quite small.

This can be achieved as follows: a suitable amount of hybridization solution and an aliquot from the reaction mixture from the amplification in which extension products present as double-strands have been converted into single strands by base denaturation are each separately or/and successively picked up in a pipette, preferably in the same pipette, physically separated from one another (so that mixing in the pipette is essentially excluded) and then ejected into a vessel which contains the solid phase.

In a preferred embodiment firstly the hybridization solution, then an air bubble and then the reaction mixture are aspirated into a pipette or a needle so that the two liquids do not mix if possible. Then the two liquids are rapidly dispensed into a vessel which contains the capture probe i.e. within a period of less than 5 sec. preferably less than 1 sec. Rapid mixture is achieved in particular by the speed of the dispensing and if desired by repeated uptake and ejection of the liquid into and out of the pipette. In this connection the rate of dispensing must be matched to the geometry of the reaction vessel e.g. in order to avoid splashing. Rapid mixing ensures that the hybridization of one strand of the extension product with capture probe can take place practically simultaneously to strand reassociation or the internal strand hybridization. The starting time for the hybridization is denoted $T_0$ and is the time at which reaction conditions have been set which allow for hybridization.

With regard to the incubation temperature it is preferably to choose one at which the capture probe can hybridize with the sense strand, preferably $\geq 5°$ C. below the melting point of this hybrid and $\geq 2°$ C. above the freezing point of the mixture.

The probe(s) are preferably incubated with the reaction mixture for between 45 and 180 min. Subsequently the fraction of primers (in particular of the labelled primer) and of labelled amplification products which has not bound to the solid phase is separated from the solid phase so that non-selectively bound i.e. excess label does not significantly interfere with the determination of the selectively bound fraction. This can be achieved by removing the liquid by pipette and can be optionally facilitated by one or several wash steps.

In a preferred embodiment of the invention relatively unstringent hybridization conditions are selected for the incubation of the capture probe with the amplificates i.e. so that selective hybridization does not yet occur but a relatively large amount of nucleic acid is relatively unselectively bound. In contrast relatively stringent hybridization conditions are selected in one or several of the subsequent wash steps. In this process, hybrids in which the capture probe is relatively less complementary to the target sequence are detached again whereas the more stringently complementary hybrids remain bound.

For this purpose the wash buffer is preferably chosen as follows: It contains 2 to 5 mol/l TMAC, 0.1–5 mmol/l of a chelating agent (e.g. EDTA), 0.1 to 5% by weight of a preferably anionic detergent and 1 to 100 mM of an organic buffer base.

The present procedure is particularly suitable for detecting mutations in particular those with a complex pattern e.g. resistances of organisms for example towards antibiotics or polymorphisms such as p53. It is characterized in that it is particularly selective i.e. can differentiate or discriminate particularly well between very similar nucleic acid sequences.

In a preferred embodiment the sample, e.g. a serum, is treated with the aid of reagents such that the nucleic acids to be detected are present in a form that is accessible for the hybridization. This can for example be achieved by the addition of reagents which lyse the cell walls of organisms e.g. viruses or bacteria. If desired the nucleic acids can be prepurified e.g. by immobilization on a solid phase e.g. glass particles with the addition of chaotropic salts. Such prepurifications are described for example in EP-A-0 389 063 or U.S. Pat. No. 5,234,809. The solution containing nucleic acids is then subjected to a nucleic acid amplification by PCR in which the reverse primer is labelled with a detectable group but not the forward primer. The region of the nucleic acid to be detected that is located between the primers is the region which contains the target sequence. The solution containing amplificate is added at the same time as a hybridization solution to a flat reaction vessel on the surface of which capture probes with different sequences are bound in discrete areas and the capture probes are each complementary to one target sequence on the unlabelled sense strand of a nucleic acid to be detected. If, in contrast, the capture probes are designed to be antiparallel complementary to the anti-sense strand, the forward primer is correspondingly used in a labelled form.

In this process the desired hybrids composed of the capture probe and the two strands are formed according to the invention provided the nucleic acid to be detected was present in the original sample. The formation of the hybrids can be detected via the label incorporated in the amplificates e.g. directly by means of a (fluorescence) microscope. In the case of indirect labelling e.g. by a hapten, labelled antibody specific to the hapten is added so that the antibody and thus the (second) label binds to the (first) label. Subsequently it is possible to measure the (second) label.

The measurement is evaluated by establishing at which positions within the array of specific reaction sites a label is measured. The sequence that is complementary to the (known) sequence of the capture probe that is bound there is then present in the sample. In order to decide whether the measured signal can be rated as positive it is usual to define a threshold value above which it is assumed that the nucleic acid was present. Since the measured signals can vary for different sequences and similarities, and the measurement sensitivity is usually so high that background signals could also be inspected as a signal, the increased power of discrimination that can be achieved by the present invention is extremely important in order to avoid false assessments. It enables a very much improved differentiation between the signals in the presence and absence of the target sequence.

In such multiple tests it is possible on the one hand to detect diverse analytes e.g. viruses such as HBV, HGV, HCV and HIV together using various primer pairs or partial sequences of a particular nucleic acid e.g. polymorphisms on human genomes but it is also possible to determine sequences by the sequencing by hybridization (SBH) method either de-novo (previously unknown sequences) or to find deviations from a normal sequence. An SBH method is described for example by Khrapko et al., FEBS Letters 250, 118–122 (1989) or Khrapko et al., J. DNA Sequencing and Mapping 1, 375–388 (1991). In this method capture probes of approximately the same length are usually used the sequences of which overlap such that they are shorter at one end and longer at the other end than the sequence of nearest similarity. The same applies for each additional sequence which are in an unchanged direction longer at one end and shorter at the other end. The shift that is formed in this manner is between 1 and 5 nucleotides according to requirements. The sequence of the nucleic acids to be sequenced can be determined by combining the hybridization information obtained.

Allele-specific or mutation-specific capture probes can be used for mutation analysis. Therefore a subject matter is also a method for the selective detection of a nucleic acid comprising the steps of amplification of the nucleic acid or of a part thereof with the aid of two primers one of which can hybridize with one strand of the nucleic acid to be detected and the other can hybridize with a complementary strand thereto and at least one of which contains a bound detectable label to form one extension product of these primers in a reaction mixture, binding a capture probe to one of these extension products to form a hybridization complex which contains the capture probe and at least this extension product, separating the extension product bound to the capture probe from non-bound components of the reaction mixture and determining the detectable label bound to the capture probe wherein the capture probe is selected such that it can bind with the strand of the extension product which can also hybridize with the extension product formed by extension of the labelled primer.

A further subject matter is a reagent kit for the detection of nucleic acids containing in separate containers at least one primer which contains a bound detectable label for the amplification of nucleic acids or parts thereof, at least two capture probes with different sequences characterized in that the primer is selected such that it can hybridize with the same strand of the extension product as the capture probes.

An additional subject matter of the invention is the use of a reagent kit containing at least one detectably labelled primer and at least 2 capture probes with different sequences wherein the at least one detectably labelled primer is selected such that it can hybridize with the same strand of each target nucleic acid as the capture probes in a mutation analysis.

The present invention is elucidated by the following examples:

EXAMPLES

Example 1

Detection Of *Mycobacterium Tuberculosum*

A. Sample Preparation and Amplification

DNA plasmid standards cloned in *E. coli* which contain the gene for the β subunit of the RNA polymerase (rpo β) of Mycobacterium tuberculosis (wild-type WT and mutants MX) were isolated after cell lysis and purified by means of small Quiagen columns. The rpo β gene segment that is relevant for rifampicin resistance was amplified by PCR in which optionally the forward or the reverse primer carried a DIG label at the 5' end. The primer oligonucleotides were synthesized according to standard phosphoramidite chemistry (Caruthers, M. H., Barone A. D., Beaucage, S. L., Dodds, D. R., Fisher, E. F., McBride, L. J., Matteucci, M., Stabinsky, Z., Tang, J. Y., Chemical synthesis of deoxyribonucleotides, Methods in Enzymology 154, 287–313 (1987)) and optionally 5' terminally functionalized by incorporation of [N-trifluoro-acetamido-(3-oxa)pentyl-N,N-diisopropyl-methyl-phsophoramidite (Boehringer Mannheim Company (BM), order No. 1480863), subsequent basic cleavage of the trifluoroacetyl protective group with aqueous ammonia and reaction with digoxigenin-3-O-methylcarbonyl-6-amidocaproyl-NHS-ester (BM Company, order No. 1333054).

The PCR temperature profile run on a Perkin-Elmer GeneAmp PCR system 9600 using 1 μl purified cell extract per 100 μl PCR reaction solution was:

Initiation 3'94° C.; 10 cycles 15" 95° C./30" 68° C./30" 72° C.; 20 cycles 15" 94° C./30" 68° C./30"+additionally 20" with each new cycle at 72° C.; 5' 70° C. Equilibration≧30' 4° C.

PCR buffer: 10 mM Tris/HCl, 1.5 mM $MgCl_2$, 50 mM KCl, pH 8.3, primer (forward and reverse, respectively, see below) polymerase and dNTPs according to PCR Core Kit (BM, catalogue No. 1578553).

```
PCR primer (R = reverse; F = forward):
primer 55F:5'-TCG CCG CGA TCA AGG AGT-3'                (SEQ ID NO.1)

primer 55R:5'-TGC ACG TCG CGG ACC TCC A-3'              (SEQ ID NO.2)

primer 56F:5'-DIG-TCG CCG CGA TCA AGG AGT-3'            (SEQ ID NO.3)

primer 56R:5'-DIG-TGC ACG TCG CGG ACC TCC A-3'          (SEQ ID NO.4)

MTB rpo-β amplicon (sense strand; 157 nt):
5'-TCG CCG CGA TCA AGG AGT TCT TCG GCA CCA GCC AGC TGA GCC  (SEQ ID NO.5)

AAT TCA TGG ACC AGA ACA ACC CGC TGT CGG GGT TGA GCC ACA AGC

GCC GAC TGT CGG CGC TGG GGC CCG GCG GTC TGT CAC GTG AGC GTG

CCG GGC TGG AGG TCC GCG ACG TGC A-3'
```

Amplified plasmid standards, wild-type (WT) or mutants (MX) were aliquoted after being checked by gel electrophoresis and ethidium bromide staining and stored deep-frozen until use.

B) Denaturation of the Amplificates

Firstly 5 μl of a solution of the DIG-labelled amplificate and 5 μl of a strongly basic denaturation solution (50 mM NaOH, 2 mM EDTA) are mixed in an inert reaction vessel (e.g. from the Eppendorf Co.) and incubated for ≧10 min at RT.

C) Manufacture of the Disposables

Capture probes that are antiparallel complementary to the sense amplicon strand were also synthesized by standard phosphoramidite chemistry as 18 mers with a 5'-terminal biotinylation. The biotin group was incorporated directly during the synthesis by means of a biotinoyl-6-amidohexyl-N,N-diisopropyl-β-cyanoethyl-phosphoramidite in which the reactive imidazolyl nitrogen is protected by dimethoxytrityl (Perkin-Elmer Company ABI, No. 401396).

```
c = complementary to the sense strand; S = sensitive (to
rifampicin treatment ( = probes detecting the wild-type);
R = resistant to rifampicin treatment ( = probes
detecting diverse mutants)
cS1-18/2-BIO  5'-BIO-T20-ATT GGC TCA GCT GGC TGG-3'  (Tab.4)     SEQ ID NO.6 cR1a-18-BIO   5'-BIO-T20-TTG GCT CGG CTG GCT GGT-3'  (Tab.4)     SEQ ID NO.7 cS2-18-BIO    5'-BIO-T20-GTT GTT CTG GTC CAT GAA-3'  (Tab.4)     SEQ ID NO.8 cR2-18-BIO    5'-BIO-T20-GTT GTT CTG GAG CAT GAA-3'  (Tab.4)     SEQ ID NO.9 cS3-18-/1-BIO 5'-BIO-T20-CAA CCC CGA CAG CGG GTT-3'  (Tab.1—3)   SEQ ID NO.10 cS3-18/2-BIO  5'-BIO-T20-TCA ACC CCG ACA GCG GGT-3'  (Tab.4)     SEQ ID NO.11 cS4-18-BIO    5'-BIO-T20-TCG GCG CTT GTG GGT CAA-3'              SEQ ID NO:12 cR4a-18-BIO   5'-BIO-T20-TCG GCG CTT GTA GGT CAA-3'              SEQ ID NO.13 cR4b-18-BIO   5'-BIO-T20-TCG GCG CTT GTC GGT CAA-3'              SEQ ID NO.14 cdS4-18-BIO   5'-BIO-T20-TCG GCG CTT GCG GGT CAA-3'  (Tab.4)     SEQ ID NO.15 cS5-18-BIO    5'-BIO-T20-CCC CAG CGC CGA CAG TCG-3'              SEQ ID NO.16 cR5-18-BIO    5'-BIO-T20-CCC CAG CGC CAA CAG TCG-3'  (Tab.4)     SEQ ID NO.17

MBD           5'-BIO-T25-DIG-Y-T-3'                  (Tab.4)     SEQ ID NO.18
BIO = monobiotinylation via on-line incorporation of
biotinoyl-6-amidohexyl phosphoramidite
Y = on-line incorporation of 3-trifluoroacetamido-1,2-
propandiole-phosphoramidite, subsequent basic deblocking,
extension with 6-aminocaproic acid NHS ester and labelling by
reaction with DIG-3-0-carboxymethyl-NHS ester (base-stable)
(see above)
MBD: control oligo for the monitoring of conjugate/detector
function.
```

Polystyrene disposables (DE-19707204.6) dyed with a black carbon pigment with a microwell measuring 0.7 cm (round, diameter)×0.15 cm (depth) served as disposables which were activated with a thermoBSA-biotin/streptavidin layer (PCT/EP89/00195). Biotin functionalized capture probes were immobilized on this by means of an inkjet printing process according to EP-A-0 268 237. Each nozzle of the printing head was filled with a capture probe solution with a different specificity to print and subsequently dry small circular reaction zones with a diameter of ca. 100 µm; (these are isolated from one another) in geometric patterns on the test carrier and thus generate an array of different capture probes (C2a solid phase).

Inkjet Printing Solution: 5 mM Mes/ 5 mM Tris-HCl, pH 7.4, 1% (w/v) sucrose, 0.5 mg/ml BSA-Res (dialysed), probe concentration 1 µM.

D) Probe Hybridization

40 µl hybridization (=neutralization) buffer and 10 µl denatured PCR amplificate were aspirated successively and separated by an air bubble using a Hamilton MicroLab dispenser and subsequently dispensed under pressure in one step into the disposable so that a rapid mixing occurs and there is an identical $T_0$ for all hybridization events. The mixture was incubated for 90 min at room temperature (tables 1 to 3) or at 37° C. (table 4), with (tables 1 to 3) or without (table 4) shaking (E. Bühler Swip, 250 rpm, linear).

Hybridization Buffer 10 mM Tris/HCl, 4 M TMAC (tetramethylammonium chloride), 1 mM EDTA, 0.1% Tween-20 [in example 4: Zwittergent 3-12] (w/v), 0.013% oxypyrion, 0.01% methylisothiazolone, pH 6.3.

E) Wash Step

Firstly 20 sec b/f separation at 59 (61)° C. (set target temperature on the manual DNA washing device) or 60° C. (actual temperature on the semiautomatic incubator/shaker/washing module) with wash solution 1 (flow rate 14.4 and 12 ml/min, respectively); immediately afterwards rewash for 20 sec with low salt wash buffer at RT (wash solution 2, flow rate 12 ml/min).

Wash Solution 1 (For The Stringent Washing Step After Hybridization)

10 mM Tris/HCl, 4 M TMAC, 1 mM EDTA, 0.1% Tween-20 [in Tab.4: Zwittergent 3-12] (w/v), 0.013% oxypyrion, 0.01% methylisothiazolone, pH 8.0.

Wash Solution 2 (to rewash for the bound/free separation after hybridization, and for the bound/free separation after the conjugate reaction):

15 mM NaCl/1.5 mM $Na_3$ citrate/0.1% SDS solution, pH 7.0

F) Conjugate Binding

30 µl conjugate suspension (anti-DIG functionalized fluorobeads in stable suspension, 0.01% solids) was pipetted into the well and the mixture was incubated for 30 min at room temperature (60 min, 37° C. in table 3). Incubation for the final DIG: anti-DIG immune reaction is performed with (E. Bühler Swip, 250 rpm, linear, tables 1 to 3) or without (table 4) shaking.

It was subsequently washed for 8 sec with low salt wash buffer (wash solution 2) at RT and at a flow rate of 12 ml/min.

Conjugate Suspension

MAB<DIG>(IgG)-110 nm COOH latex fluorobead suspension (prepared from BM biochemicals beads cat. No. 1742582, used according to U.S. Pat. No. 5,516,635) 0.1% by weight solids is prepared by dissolving a bottle of conjugate lyophilisate with 200 µl redistilled water. The daily portions are prepared by 1:10 dilution to 0.01% solids in conjugate buffer.

Conjugate Buffer 50 mM Tris/HCl, pH 8.5, 150 mM NaCl, 0.5% RPLA-IV, 10 µg/ml M-IgG-1 (poly-Fab, BM, Biochemicals for the Diagnostic Industry, cat. No. 1368388), 10 µg/ml M-IgG-2a (poly-Fab, BM, Biochemicals for the Diagnostic Industry, cat. No. 1866729), 0.05% (w/v) Tween-20, 0.095% $NaN_3$.

G) Measurement of the Bound Fluorescence and Evaluation

The detection was carried out using a microscope/CCD camera construction from Leica Company (Heidelberg, GFR).

The measured results are compiled in tables 1–3 which were obtained with the initial 5×(5 probe) array with a comparative evaluation of F amplicons (=sense strands labelled via forward primers) and R amplicons (=antisense strands labelled via reverse primers) with a manual test procedure. The wash temperature in the stringent washing step after hybridization, and the incubation temperature and time for the conjugate reaction were varied.

TABLE 1

5x array

Characteristics: washing with wash buffer 1; 59° C. (20 sec addition of wash buffer) conjugate 30 min shaking/RT Results:

Solid phase with various probes in separate spots

| Sample | cS3 | CV(2) | cS4 | CV(2) | cR4a | CV(2) | cR4b | CV(2) | cS5 | CV(2) |
|---|---|---|---|---|---|---|---|---|---|---|
| R-WT | | 12.5% | | 7.3% | 94 | 9.8% | 44 | 8.6% | | 6.1% |
| R-dS4 | | 13.6% | 95 | 34.4% | 29 | 9.5% | | | | 12.5% |
| R-R4a | | 15.3% | 321 | 22.8% | | 5.9% | 130 | 5.8% | | 4.2% |
| R-R4b | | 15.5% | 118 | 8.1% | 199 | 8.4% | | 4.8% | | 3.5% |
| R-R5 | | 14.0% | | 13.0% | 72 | 10.3% | 38 | 7.3% | 165 | 6.3% |
| F-/R-WT | | 7.1% | | 8.8% | 145 | 12.0% | 65 | 10.3% | | 9.8% |
| F-WT | | 13.8% | | 22.9% | 117 | 23.1% | 57 | 19.6% | | 19.1% |
| F-dS4 | | 5.5% | 237 | 22.3% | 45 | 8.1% | 43 | 5.0% | | 10.6% |
| F-R4a | | 12.6% | 419 | 4.8% | | 2.7% | 89 | 5.8% | | 1.4% |
| F-R4b | | 12.3% | 103 | 21.6% | 260 | 22.1% | | 21.9% | | 15.8% |
| F-R5 | | 4.9% | | 8.8% | 109 | 7.8% | 54 | 6.6% | 631 | 10.8% |

| Sample | Solid phase | | | |
|---|---|---|---|---|
| | cS4 | cR4a | cR4b | cS5 |
| R-WT | | 2.2% | 1.0% | |
| R-dS4 | 2.2% | 0.7% | 0.5% | |
| R-R4a | 4.1% | | 1.7% | |
| R-R4b | 3.5% | 5.9% | | |
| R-R5 | | 1.3% | 0.7% | ca. 0.09 x WT |
| F-/R-WT | | 2.6% | 1.1% | |
| F-WT | | 2.6% | 1.2% | |
| F-dS4 | 5.2% | 1.0% | 0.9% | |
| F-R4a | 7.8% | | 1.7% | |
| F-R4b | 4.0% | 10.0% | | |
| F-R5 | | 1.4% | 0.7% | ca. 0.19 x WT |

The squares shaded grey represent a hybridization event with an exactly complementary probe.

TABLE 2

5x Array

Characteristics: washing with wash buffer 1; 61° C. (20 sec addition of washing buffer) 30 min shaking/RT Solid phase with various probes in separate spots

| Sample | cS3 | CV(2) | cS4 | CV(2) | cR4a | CV(2) | cR4b | CV(2) | cS5 | CV(2) |
|---|---|---|---|---|---|---|---|---|---|---|
| R-WT |  | 16.5% |  | 9.3% | 140 | 18.5% | 62 | 12.2% |  | 3.2% |
| R-dS4 |  | 9.2% | 215 | 15.4% | 32 | 9.1% | 30 | 8.9% |  | 8.0% |
| R-R4a |  | 19.7% | 423 | 7.6% |  | 7.6% | 136 | 13.7% |  | 5.7% |
| R-R4b |  | 15.5% | 154 | 18.1% | 238 | 13.7% |  | 4.7% |  | 2.8% |
| R-R5 |  | 26.0% |  | 12.8% | 77 | 10.5% | 37 | 8.4% | 127 | 7.0% |
| F-/R-WT |  | 19.3% |  | 8.2% | 115 | 8.3% | 52 | 9.4% |  | 10.1% |
| F-WT |  | 14.8% |  | 7.2% | 87 | 10.0% | 44 | 6.8% |  | 3.3% |
| F-dS4 |  | 14.6% | 167 | 6.8% | 39 | 9.5% | 42 | 4.7% |  | 6.5% |
| F-R4a |  | 9.5% | 349 | 13.0% |  | 4.6% | 76 | 6.6% |  | 6.5% |
| F-R4b |  | 13.3% | 85 | 32.8% | 155 | 27.2% |  | 22.1% |  | 12.8% |
| F-R5 |  | 22.8% |  | 5.7% | 108 | 4.7% | 45 | 6.0% | 256 | 10.4% |

| Sample | Solid phase | | | |
|---|---|---|---|---|
|  | cS4 | cR4a | cR4b | cS5 |
| R-WT |  | 2.4% | 1.1% |  |
| R-dS4 | 3.7% | 0.5% | 0.5% |  |
| R-R4a | 5.0% |  | 1.6% |  |
| R-R4b | 1.8% | 5.3% |  |  |
| R-R5 |  | 1.3% | 0.6% | ca.0.04 x WT |
| F-/R-WT |  | 3.2% | 1.5% |  |
| F-WT |  | 4.0% | 2.0% |  |
| F-dS4 | 7.8% | 1.8% | 2.0% |  |
| F-R4a | 10.9% |  | 2.4% |  |
| F-R4b | 5.1% | 9.3% |  |  |
| F-R5 |  | 1.5% | 0.6% | ca. 0.07 x WT |

TABLE 3

5x array

Characteristics: washing with wash buffer 1; 61° C. (20 sec addition of washing buffer) 60 min shaking/37° C.

Results

Solid phase with various probes in separate spots

| Sample | cS3 | CV(2) | cS4 | CV(2) | cR4a | CV(2) | cR4b | CV(2) | cS5 | CV(2) |
|---|---|---|---|---|---|---|---|---|---|---|
| R-WT |  | 2.1% |  | 9.3% | 382 | 3.0% | 354 |  |  | 2.5% |
| R-dS4 |  | 4.5% | 428 | 6.4% | 378 |  | 378 |  |  | 13.9% |
| R-R4a |  | 2.2% | 581 | 8.4% |  | 5.9% | 464 | 2.5% |  | 2.6% |
| R-R4b |  |  | 462 | 3.9% | 498 | 1.7% |  | 4.1% |  | 5.0% |
| R-R5 |  | 2.6% |  | 9.4% | 399 | 3.0% | 354 |  | 410 | 1.5% |
| F-/R-WT |  | 4.2% |  | 4.8% | 515 | 4.0% | 429 | 9.2% |  | 1.3% |
| F-WT |  |  |  | 36.4% | 356 |  | 356 |  |  | 57.9% |
| F-dS4 |  | 5.4% | 481 | 6.7% | 348 |  | 348 |  |  | 4.0% |
| F-R4a |  | 3.4% | 574 | 7.5% |  | 7.4% | 391 | 4.4% |  | 4.0% |
| F-R4b |  | 2.8% | 430 | 4.3% | 464 | 1.9% |  |  |  | 2.9% |
| F-R5 |  | 2.4% |  | 6.2% | 421 | 1.9% | 366 |  | 520 | 2.3% |

| | Solid phase | | | |
|---|---|---|---|---|
| Sample | cS4 | cR4a | cR4b | cS5 |
| R-WT |  | 13.7% | 12.7% |  |
| R-dS4 | 15.3% | 13.5% | 13.5% |  |
| R-R4a | 5.7% |  | 4.6% |  |
| R-R4b | 12.3% | 13.2% |  |  |
| R-R5 |  | 4.8% | 4.3% | 23.2% |
| F-/R-WT |  | 6.5% | 5.4% |  |
| F-WT |  | 44.0% | 44.0% |  |
| F-dS4 | 59.5% | 43.0% | 43.0% |  |
| F-R4a | 19.0% |  | 13.0% |  |
| F-R4b | 16.3% | 17.6% |  |  |
| F-R5 |  | 3.8% | 3.3% | 34.4% |

Table 4 shows the same for the extended 12x(12 probe) array under the conditions: 90 min hybridization at 37° C., 30 min conjugate reaction at RT, probe washing step at 60° C. for 20 sec carried out on a semi-automatic DNA incubator/shaker/washing module. At this time the test was not optimized for the newly added regions 1 and 2 so that primarily the regions 4 and 5 (as in the smaller initial array) should be considered. The position of the regions is shown in FIG. 3.

TABLE 4

12X Array

R-amplicon

Solid phase with various robes in separate spots

| Sample No | Name | cS3 | cS4 | cR4a | cR4b | cdS4 | cS5 | cR5 |
|---|---|---|---|---|---|---|---|---|
| 3 | WT3.11 |  |  | 2.1% | 0.5% | 7.1% |  | 0.8% |
| 4 | WT3.11 |  |  | 2.4% | 0.3% | 5.2% |  | 1.2% |
| 5 | R1a |  |  | 0.5% | 0.2% | 1.2% |  | 2.1% |

TABLE 4-continued
| | | | | | | | |
|---|---|---|---|---|---|---|---|
| 6 | R1a |  | 0.4% | 0.2% | 2.6% |  | 2.8% |
| 7 | R2 |  | 0.4% | 0.1% | 0.4% |  | 1.1% |
| 8 | R2 |  | 0.4% | 0.1% | 0.8% |  | 1.5% |
| 9 | R4a | 12.9% |  | 1.5% | 2.0% |  | 0.9% |
| 10 | R4a | 13.1% |  | 3.3% | 5.3% |  | 3.1% |
| 11 | R4b | 14.3% | 7.9% |  | 9.6% |  | 2.7% |
| 12 | R4b | 7.4% | 4.2% |  | 5.2% |  | 0.8% |
| 13 | dS4 | 19.1% | 0.5% | 0.2% |  |  | 1.3% |
| 14 | dS4 | 15.5% | 0.4% | 0.1% |  |  | 0.6% |
| 15 | R5 |  | 2.5% | 2.3% | 14.2% | 0.4% |  |
| 16 | R5 |  | 1.5% | 0.7% | 9.0% | 1.4% |  |
| 17 | WTF/R-amp. |  | 6.8% | 1.2% | 10.4% |  | 3.2% |
| 18 | WTF/R-amp. |  | 4.9% | 1.1% | 22.1% |  | 1.8% |
| 19 | WT3.11 |  | 3.0% | 0.3% | 8.2% |  | 1.0% |
| 20 | WT3.11 |  | 3.0% | 0.6% | 20.4% |  | 0.6% |
F-amplicon
| | | Solid phase with various robes in separate spots | | | | | | |
|---|---|---|---|---|---|---|---|---|
| Sample No | Name | cS3 | cS4 | cR4a | cR4b | cdS4 | cS5 | cR5 |
| 3 | WT3.11 |  | 4.6% | 1.0% | 20.3% |  | 3.4% | |
| 4 | WT3.11 |  | 7.6% | 2.6% | 18.2% |  | 2.8% | |
| 5 | R1a |  | 0.5% | 0.2% | 1.7% |  | 1.5% | |
| 6 | R1a |  | 0.8% | 0.5% | 0.9% |  | 3.4% | |
| 7 | R2 |  | 1.7% | 0.1% | 5.3% |  | 3.6% | |
| 8 | R2 |  | 3.4% | 0.6% | 2.6% |  | 5.8% | |
| 9 | R4a | | 53.6% |  | 2.4% | 1.4% |  | 4.1% |
| 10 | R4a | | 90.4% |  | 1.2% | 5.8% |  | 2.4% |
| 11 | R4b | | 29.3% | 15.5% |  | 15.3% |  | 8.3% |
| 12 | R4b | | 54.7% | 25.9% |  | 16.6% |  | 8.9% |
| 13 | dS4 | | 50.4% | 1.8% | 0.7% |  |  | 1.8% |

TABLE 4-continued

| | | | | | | | | |
|---|---|---|---|---|---|---|---|---|
| 14 | dS4 | 51.0% | 2.3% | 0.5% | | | | 0.3% |
| 15 | R5 | | 10.9% | 12.3% | 5.6% | 6.2% | | |
| 16 | R5 | | 1.9% | 0.4% | 3.6% | 2.4% | | |
| 17 | WTF/R-amp. | | 5.8% | 2.8% | 17.8% | | | 1.8% |
| 18 | WTF/R-amp. | | 5.5% | 0.7% | 24.6% | | | 2.3% |
| 19 | WT3.11 | | 6.4% | 2.6% | 6.4% | | | 3.3% |
| 20 | WT3.11 | | 4.5% | 0.6% | 21.9% | | | 1.1% |

In all cases it is clear that the use of R-amplicons i.e. an indirect detection via the strand reassociation complex surprisingly enables a significantly better discrimination to be achieved than with a direct detection of probe-bound F-amplicons.

This surprising effect applies in particular when single-stranded analyte DNA or RNA has a strong tendency for internal strand secondary structure formation so that spatial reorientation processes influence the accessibility of the group to be detected. This is the case for the amplified rpo β-gene segment (see FIG. 4:2D folding proposal according to an algorithm of Dr. Zuker, Washington University; Institute for Biomedical Computing). In FIG. 5 an attempt was made to illustrate the situation in which (unlike in the present invention) the capture probe would directly hybridize with the labelled strand in the case of internal strand reassociation (situation A) or no internal strand reassociation (situation B).

What is claimed is:

1. A method for the detection of a nucleic acid comprising the steps:

a) amplifying the nucleic acid or a part thereof in a reaction mixture with a first primer and a second primer, one of which can hybridize with one strand of the nucleic acid to be detected and the other of which can hybridize with a strand complementary thereto, wherein one of the primers contains a detectable label, to form a labeled extension product and an unlabeled extension product which are complementary to each other;

b) contacting a capture probe with the extension products to form a hybridization complex wherein the complex is necessarily a duplex, said hybridization complex comprising the capture probe, the labeled extension product and the unlabeled extension product, wherein the capture probe is selected such that the capture probe hybridizes to only the unlabeled extension product and only the unlabeled extension product hybridizes with the labeled extension product;

c) separating the hybridization complex from other components of the reaction mixture; and d) determining the detectable label in the hybridization complex of step b).

2. The method of claim 1, wherein the capture probe is bound to a solid phase.

3. The method of claim 2, wherein the hybridization complex comprising the solid phase-bound capture probe is visualized by a detection reagent that i) provides a signal or generates a signal and ii) contains a component capable of binding to the primer label.

4. The method of claim 3, wherein the detection reagent contains a particulate signal-transmitting or signal mediating component.

5. A method for the selective detection of specific sequences in one or several nucleic acids(s) from a sample comprising the steps:

a) amplifying the nucleic acids or parts thereof in a reaction mixture with at least one set of two primers, wherein a first primer in each set of primers can hybridize with one strand of the nucleic acid(s) and a second primer in each set can hybridize with a strand complementary thereto, wherein one of the first and second primers contains a detectable label, to form a labeled extension product and an unlabeled extension product which are complementary to each other for each of the specific sequences;

b) contacting at least one capture probe with the extension products to form hybridization complexes wherein the complexes are necessarily duplexes, said hybridization complexes comprising a capture probe, the labeled extension product and the unlabeled extension product for each of the specific sequences, wherein the capture probe is selected such that the capture probe hybridizes to only the unlabeled extension product and only the unlabeled extension product hybridizes with the labeled extension product;

c) separating the hybridization complexes from other components of the reaction mixture; and d) determining the detectable label in the hybridization complexes of step b).

6. The method of claim 5, comprising at least two distinct capture probes which are bound to spatially separate, discrete areas of a solid phase.

7. The method of claim 5, wherein the labeled probe is used to form extension products from a plurality of specific sequences.

8. The method of claim 6, wherein the at least one detectably labeled primer is selected such that it can hybridize with the same strand of each target nucleic acid as the capture probes in a mutation analysis.

9. The method of claim 1, wherein in said contacting step b), the extension products are provided in single-stranded form.

10. The method of claim 9, wherein in said contacting step b), conditions are chosen such that hybridization for the unlabeled extension product with the capture probe occurs practically simultaneously with hybridization of the unlabeled extension product with the labeled extension product.

11. The method of claim 9, wherein the extension products are provided in single-stranded form by converting double-stranded extension products into single-stranded extension products by alkaline denaturaton, and the method further comprises the step of neutralizing the alkaline before the extension products are contacted with the capture probe.

* * * * *

SEQUENCE LISTING

<160> NUMBER OF SEQ ID NOS: 18

<210> SEQ ID NO 1
<211> LENGTH: 18
<212> TYPE: DNA
<213> ORGANISM: Mycobacterium tuberculosis

<400> SEQUENCE: 1
tcgccgcgat caaggagt                                          18

<210> SEQ ID NO 2
<211> LENGTH: 19
<212> TYPE: DNA
<213> ORGANISM: Mycobacterium tuberculosis

<400> SEQUENCE: 2
tgcacgtcgc ggacctcca                                         19

<210> SEQ ID NO 3
<211> LENGTH: 18
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate ester with digoxigenin

<400> SEQUENCE: 3
tcgccgcgat caaggagt                                          18

<210> SEQ ID NO 4
<211> LENGTH: 19

```
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate ester with digoxigenin

<400> SEQUENCE: 4
tgcacgtcgc ggacctcca                                              19

<210> SEQ ID NO 5
<211> LENGTH: 157
<212> TYPE: DNA
<213> ORGANISM: Mycobacterium tuberculosis

<400> SEQUENCE: 5
tcgccgcgat caaggagttc ttcggcacca gccagctgag ccaattcatg gaccagaaca    60
acccgctgtc ggggttgacc cacaagcgcc gactgtcggc gctggggccc ggcggtctgt   120
cacgtgagcg tgccgggctg gaggtccgcg acgtgca                            157

<210> SEQ ID NO 6
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 6
tttttttttt tttttttttt attggctcag ctggctgg                            38

<210> SEQ ID NO 7
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 7
tttttttttt tttttttttt ttggctcggc tggctggt                            38

<210> SEQ ID NO 8
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 8
tttttttttt tttttttttt gttgttctgg tccatgaa                            38

<210> SEQ ID NO 9
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 9
```

```
tttttttttt tttttttttt gttgttctgg agcatgaa                    38
```

<210> SEQ ID NO 10
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 10

```
tttttttttt tttttttttt caaccccgac agcgggtt                    38
```

<210> SEQ ID NO 11
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 11

```
tttttttttt tttttttttt tcaaccccga cagcgggt                    38
```

<210> SEQ ID NO 12
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 12

```
tttttttttt tttttttttt tcggcgcttg tgggtcaa                    38
```

<210> SEQ ID NO 13
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 13

```
tttttttttt tttttttttt tcggcgcttg taggtcaa                    38
```

<210> SEQ ID NO 14
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 14

```
tttttttttt tttttttttt tcggcgcttg tcggtcaa                    38
```

<210> SEQ ID NO 15
<211> LENGTH: 38
<212> TYPE: DNA
<213> ORGANISM: Mycobacterium tuberculosis
<220> FEATURE:
<221> NAME/KEY: misc_signal -continued

```
<222> LOCATION: (1)..(1)
<223> OTHER INFORMATION: Phosphate linked to biotin via Aminolinker

<400> SEQUENCE: 15
tttttttttt tttttttttt tcggcgcttg cgggtcaa                    38

<210> SEQ ID NO 16
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 16
tttttttttt tttttttttt ccccagcgcc gacagtcg                    38

<210> SEQ ID NO 17
<211> LENGTH: 38
<212> TYPE: DNA
<213> ORGANISM: Mycobacterium tuberculosis
<220> FEATURE:
<221> NAME/KEY: misc_signal
<222> LOCATION: (1)..(1)
<223> OTHER INFORMATION: Phosphate linked to biotin via Aminolinker

<400> SEQUENCE: 17
tttttttttt tttttttttt ccccagcgcc aacagtcg                    38

<210> SEQ ID NO 18
<211> LENGTH: 27
<212> TYPE: DNA
<213> ORGANISM: Mycobacterium tuberculosis
<220> FEATURE:
<221> NAME/KEY: misc_signal
<222> LOCATION: (27)..(27)
<223> OTHER INFORMATION: Y means incorporation of Aminolinker-
      phosphoramidite subsequently
         estered with 3-O carboxymethyl digoxigenin

<400> SEQUENCE: 18
tttttttttt tttttttttt tttttyt                                27
```